US008349877B2

(12) United States Patent
Brix et al.

(10) Patent No.: US 8,349,877 B2
(45) Date of Patent: Jan. 8, 2013

(54) TERNARY FUNGICIDAL COMPOSITIONS COMPRISING BOSCALID AND CHLOROTHALONIL

(75) Inventors: Horst Dieter Brix, Landau (DE); Daniel Ebersold, Neustadt/Weinstr (DE); Martin Semar, Gleiszellen-Gleishorbach (DE); Jens Bruns, Neustadt (DE); Michael Vonend, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 150 days.

(21) Appl. No.: 12/679,523

(22) PCT Filed: Sep. 25, 2008

(86) PCT No.: PCT/EP2008/062851
§ 371 (c)(1),
(2), (4) Date: Mar. 23, 2010

(87) PCT Pub. No.: WO2009/040397
PCT Pub. Date: Apr. 2, 2009

(65) Prior Publication Data
US 2010/0197741 A1 Aug. 5, 2010

(30) Foreign Application Priority Data
Sep. 26, 2007 (EP) .................................. 07117274

(51) Int. Cl.
*A01P 3/00* (2006.01)
*A01N 25/26* (2006.01)
*A01N 43/40* (2006.01)
(52) U.S. Cl. ... 514/355; 514/354; 514/525; 514/259.31; 514/561; 514/551; 504/100; 424/637
(58) Field of Classification Search .................. 514/355, 514/354, 525, 259.31, 561, 551; 504/100; 424/637
See application file for complete search history.

(56) References Cited

U.S. PATENT DOCUMENTS

| 6,410,572 | B1 * | 6/2002 | Schelberger et al. | 514/355 |
| 2003/0078301 | A1 * | 4/2003 | Cohen et al. | 514/561 |
| 2011/0136665 | A1 * | 6/2011 | Tormo i Blasco et al. | 504/100 |

FOREIGN PATENT DOCUMENTS
WO   WO 99/31983   7/1999

OTHER PUBLICATIONS

International Search Report for International Application No. PCT/EP2008/062851.
International Preliminary Report on Patentability for International Application No. PCT/EP2008/062851.
Worthing et al., "The Pesticide Manual, Tenth Edition Ed", (1995), pp. 1335-1341, XP002031460 Search Report.

* cited by examiner

*Primary Examiner* — Savitha Rao
(74) *Attorney, Agent, or Firm* — Brinks, Hofer, Gilson & Lione

(57) ABSTRACT

Ternary fungicidal compositions comprising as active components
1) boscalid,
2) chlorothalonil and
3) at least one active compound III, selected from groups A) to F):
A) azoles;
B) strobilurins;
C) carboxamides;
D) heterocyclic compounds;
E) carbamates;
F) other fungicides;
in a synergistically effective amount, methods for controlling phytopathogenic harmful fungi using compositions of boscalid, chlorothalonil and at least one active compound III, the use of boscalid and chlorothalonil with at least one active compound III for preparing such compositions, and also agents and seed comprising such compositions.

12 Claims, No Drawings

US 8,349,877 B2

TERNARY FUNGICIDAL COMPOSITIONS COMPRISING BOSCALID AND CHLOROTHALONIL

This application is a National Stage application of International Application No. PCT/EP2008/062851 filed Sep. 25, 2008, the entire contents of which is hereby incorporated herein by reference. This application also claims the benefit under 35 U.S.C. §119 of European Patent Application No. 07117274.6, filed Sep. 26, 2007, the entire contents of which is hereby incorporated herein by reference.

The present invention relates to ternary fungicidal compositions comprising as active components
1) boscalid,
2) chlorothalonil and
3) at least one fungicidally active compound III selected from groups A) to F):
   A) azoles selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole, azaconazole, diniconazole-M, oxpoconazol, paclobutrazol, uniconazol, 1-(4-chloro-phenyl)-2-([1,2,4]triazol-1-yl)-cycloheptanol and imazalil-sulfphate;
   B) strobilurins selected from the group consisting of azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)-carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxy-phenyl)-cyclopropanecarboximidoyl-sulfanylmethyl)-phenyl)-acrylic acid methyl ester;
   C) carboxamides selected from the group consisting of carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxyphenyl)ethyl)-2-methanesulfonyl-amino-3-methylbutyramide, N-(2-(4-[3-(4-chlorophenyl)prop-2-ynyloxy]-3-methoxyphenyl)ethyl)-2-ethanesulfonylamino-3-methylbutyramide, methyl 3-(4-chlorophenyl)-3-(2-isopropoxy-carbonyl-amino-3-methyl-butyrylamino)propionate, N-(4'-bromobiphenyl-2-yl)-4-difluoromethyl-2-methylthiazole-5-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3',4'-dichloro-4-fluorobiphenyl-2-yl)-3-difluoro-methyl-1-methyl-pyrazole-4-carboxamide, N-(3',4'-dichloro-5-fluorobiphenyl-2-yl)-3-difluoromethyl-1-methylpyrazole-4-carboxamide and N-(2-cyanophenyl)-3,4-dichloro-isothiazole-5-carboxamide, 2-amino-4-methyl-thiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluoro-biphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluoro-biphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofam, N-(6-methoxy-pyridin-3-yl)cyclopropanecarboxamide, 2-iodo-N-phenyl-benzamide, N-(2-bicyclo-propyl-2-yl-phenyl)-3-difluormethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-yl-carboxamide, N-(3',4',5'-trifluorobiphenyl-2-yl)-5-chloro-1,3-dimethylpyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'- trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-3-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-3-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-3-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-3-difluoromethyl-1H-pyrazole-4-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[4'-(trifluoromethylthio)-biphenyl-2-yl]-3-difluoromethyl-1-methyl-1H-pyrazole-4-carboxamide and N-[4'-(trifluoromethylthio)-biphenyl-2-yl]-1-methyl-3-trifluoromethyl-1-methyl-1H-pyrazole-4-carboxamide;

D) heterocyclic compounds selected from the group consisting of fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methyl-piperidin-1-yl)-6-(2,4,6-trifluorophenyl)-[1,2,4]triazolo[1,5-a]pyrimidine, anilazine, diclomezine, pyroquilon, proquinazid, tricyclazole, 2-butoxy-6-iodo-3-propylchroman-4-one, acibenzolar-5-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl-[1,2,4]triazolo[1,5-a]pyrimidin-2,7-diamine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro-pyridin-2-yl)-methyl)-2,4-dichloro-nicotinamide, diflumetorim, nitrapyrin, dodemorph-acetate, fluoroimid, blasticidin-S, chinomethionat, debacarb, difenzoquat, difenzoquat-methylsulphat, oxolinic acid and piperalin;

E) carbamates selected from the group consisting of mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)-ethanesulfonyl)but-2-yl)carbamate, methyl 3-(4-chloro-phenyl)-3-(2-isopropoxycarbonylamino-3-methyl-butyrylamino)propanoate and carbamate oxime ethers of the formula IV

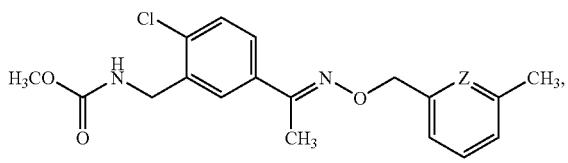

IV in which Z is N or CH;

F) other fungicides selected from the group consisting of guanidine, dodine, dodine free base, iminoctadine, guazatine,
antibiotics: kasugamycin, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts,
organophosphorus compounds: edifenphos, iprobenfos, fosetyl, fosetyl-aluminum, phosphorous acid and its salts, pyrazophos, tolclofosmethyl,
organochlorine compounds: dichlofluanid, flusulfamide, hexachloro-benzene, phthalide, pencycuron, quintozene, thiophanate-methyl, tolylfluanid,
inorganic active compounds: Bordeaux mixture, copper acetate, copper hydroxide, copper oxychloride, basic copper sulfate, sulfur,
others: cyflufenamid, cymoxanil, dimethirimol, ethirimol,
furalaxyl, metrafenone and spiroxamine, guazatine-acetate, iminoctadine-triacetate, iminoctadine-tris(albesilate), kasugamycin-hydrochlorid-hydrat, dichlorophen, pentachlorophenol and its salts, N-(4-chloro-2-nitro-phenyl)-N-ethyl-4-methyl-benzenesulfonamide, dicloran, nitrothal-isopropyl, tecnazen, biphenyl, bronopol, diphenylamine, mildiomycin, oxin-copper, prohexadione calcium, N-(cyclopropylmethoxyimino-(6-difluoromethoxy-2,3-difluoro-phenyl)methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5- dimethyl-phenyl)-N-ethyl-N-methyl formamidine, N'-(2-methyl-5-trifluormethyl-4-(3-trimethylsilanyl-propoxy)-phenyl)-N-ethyl-N-methyl formamidine and N'-(5-difluoromethyl-2-methyl-4-(3-trimethylsilanyl-propoxy)-phenyl)-N-ethyl-N-methyl formamidine;

in a synergistically effective amount.

Moreover, the invention relates to a method for controlling phytopathogenic harmful fungi using mixtures of boscalid and chlorothalonil with a fungicidally active compound III and to the use of the boscalid and chlorothalonil with III for preparing such mixtures, and to compositions and seed comprising these mixtures.

Boscalid (cf. EP-A 545099) and chlorothalonil are well known and commercially available. Compositions of boscalid and various other fungicides have already been described in the literature. The combination of boscalid and chlorothalonil is taught in WO 99/31983.

The active compounds III mentioned above, their preparation and their action against harmful fungi are generally known (cf.: http://www.hclrss.demon.co.uk/index.html); they are commercially available and known, for example, from the following references:

benalaxyl, methyl N-(phenylacetyl)-N-(2,6-xylyl)-DL-alaninate (DE 29 03 612), metalaxyl, methyl N-(methoxyacetyl)-N-(2,6-xylyl)-DL-alaninate (GB 15 00 581); ofurke, (RS)-α-(2-chloro-N-2,6-xylylacetamido)-γ-butyrolactone [CAS RN 58810-48-3];

oxadixyl; N-(2,6-dimethylphenyl)-2-methoxy-N-(2-oxo-3-oxazolidinyl)acetamide (GB 20 58 059);

aldimorph, "4-alkyl-2,5(or 2,6)-dimethylmorpholine", comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" also includes octyl, decyl, tetradecyl and hexadecyl, with a cis/trans ratio of 1:1 [CAS RN 91315-15-0];

dodine, 1-dodecylguanidinium acetate (Plant Dis. Rep., Vol. 41, p. 1029 (1957));

dodemorph, 4-cyclododecyl-2,6-dimethylmorpholine (DE 1198125);

fenpropimorph, (RS)-cis-4-[3-(4-tert-butylphenyl)-2-methylpropyl]-2,6-dimethyl-morpholine (DE 27 52 096);

fenpropidin, (RS)-1-[3-(4-tert-butylphenyl)-2-methylpropyl]piperidine (DE 27 52 096);

guazatine, mixture of the reaction products from the amidation of technical grade iminodi(octamethylene)diamine, comprising various guanidines and polyamines [CAS RN 108173-90-6];

iminoctadine, 1,1'-iminodi(octamethylene)diguanidine (Congr. Plant Pathol., 1, p. 27 (1968));

spiroxamine, (8-tert-butyl-1,4-dioxaspiro[4.5]dec-2-yl)diethylamine (EP-A 281 842);

tridemorph, 2,6-dimethyl-4-tridecylmorpholine (DE 11 64 152);

pyrimethanil, 4,6-dimethylpyrimidin-2-ylphenylamine (DD-A 151 404);

mepanipyrim, (4-methyl-6-prop-1-ynylpyrimidin-2-yl)phenylamine (EP-A 224 339);

cyprodinil, (4-cyclopropyl-6-methylpyrimidin-2-yl)phenylamine (EP-A 310 550);

cycloheximid, 4-{(2R)-2-[(1S,3S,5S)-3,5-dimethyl-2-oxocyclohexyl]-2-hydroxyethyl}piperidine-2,6-dione [CAS RN 66-81-9];

griseofulvin, 7-chloro-2',4,6-trimethoxy-6'-methylspiro[benzofuran-2(3H), 1'-cyclohex-2'-ene]-3,4'-dione [CAS RN 126-07-8];

kasugamycin, 3-O-[2-amino-4-[(carboxylminomethyl)amino]-2,3,4,6-tetradeoxy-α-D-arabino-hexopyranosyl]-D-chiro-inositol [CAS RN 6980-18-3];

natamycin, (8E,14E,16E,18E,20E)-(1R,3S,5R,7R,12R,22R,24S,25R,26S)-22-(3-amino-3,6-dideoxy-13-D-mannopyranosyloxy)-1,3,26-trihydroxy-12-methyl-10-oxo-6,11,28-trioxatricyclo[22.3.1.0$^{5,7}$]octacosa-8,14,16,18,20-pentaene-25-carboxylic acid [CAS RN 7681-93-8];

polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-3-D-allofuranuronic acid [CAS RN 22976-86-9];

streptomycin, 1,1'-{1-L-(1,3,5/2,4,6)-4-[5-deoxy-2-O-(2-deoxy-2-methylamino-α-L-glucopyranosyl)-3-C-formyl-α-L-lyxofuranosyloxy]-2,5,6-trihydroxycyclohex-1,3-ylene}diguanidine (J. Am. Chem. Soc. Vol. 69, p. 1234 (1947));

bitertanol, β-([1,1'-biphenyl]-4-yloxy)-α-(1,1-dimethylethyl)-1H-1,2,4-triazole-1-ethanol (DE 23 24 020), bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459);

cyproconazole, 2-(4-chlorophenyl)-3-cyclopropyl-1-[1,2,4]triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575);

enilconazole (imazalil), 1-[2-(2,4-dichlorophenyl)-2-(2-propenyloxy)ethyl]-1H-imidazole (Fruits, 1973, Vol. 28, p. 545);

epoxiconazole, (2RS,3SR)-1-[3-(2-chlorophenyl)-2,3-epoxy-2-(4-fluorophenyl)propyl]-1H-1,2,4-triazole (EP-A 196 038);

fenbuconazole, α-[2-(4-chlorophenyl)ethyl]-α-phenyl-1H-1,2,4-triazole-1-propanenitrile (Proc. 1988 Br. Crop Prot. Conf. Pests Dis. Vol. 1, p. 33);

fluquinconazole, 3-(2,4-dichlorophenyl)-6-fluoro-2-[1,2,4]-triazol-1-yl-3H-quinazolin-4-one (Proc. Br. Crop Prot. Conf.—Pests Dis., 5-3, 411 (1992));

flusilazole, 1-{[bis-(4-fluorophenyOmethylsilanyl]methyl}-1H-[1,2,4]triazole (Proc. Br. Crop Prot. Conf.—Pests Dis., 1, 413 (1984));

flutriafol, α-(2-fluorophenyl)-α-(4-fluorophenyl)-1H-1,2,4-triazole-1-ethanol (EP 15 756);

hexaconazole, 2-(2,4-dichlorophenyl)-1-[1,2,4]triazol-1-yl-hexan-2-ol (CAS RN 79983-71-4);

ipconazole, 2-[(4-chlorophenyl)methyl]-5-(1-methylethyl)-1-(1H-1,2,4-triazol-1-yl-methyl)cyclopentanol (EP 267 778), metconazole, 5-(4-chlorobenzyl)-2,2-dimethyl-1-[1,2,4]triazol-1-ylmethylcyclopentanol (GB 857 383);

myclobutanil, 2-(4-chlorophenyl)-2-[1,2,4]triazol-1-ylmethylpentanenitrile (CAS RN 88671-89-0);

penconazole, 1-[2-(2,4-dichlorophenyl)pentyl]-1H-[1,2,4]triazole (Pesticide Manual, 12th Ed. (2000), S. 712);

propiconazole, 1-[[2-(2,4-dichlorophenyl)-4-propyl-1,3-dioxolan-2-yl]methyl]-1H-1,2,4-triazole (BE 835 579);

prochloraz, N-(propyl-[2-(2,4,6-trichlorophenoxy)ethyl])imidazole-1-carboxamide (U.S. Pat. No. 3,991,071);

prothioconazole, 2-[2-(1-chlorocyclopropyl)-3-(2-chlorophenyl)-2-hydroxypropyl]-2,4-dihydro-[1,2,4]triazole-3-thione (WO 96/16048);

simeconazole, α-(4-fluorophenyl)-α-[(trimethylsilyl)methyl]-1H-1,2,4-triazole-1-ethanol [CAS RN 149508-90-7], tebuconazole, 1-(4-chlorophenyl)-4,4-dimethyl-3-[1,2,4]triazol-1-ylmethylpentan-3-ol (EP-A 40 345);

tetraconazole, 1-[2-(2,4-dichlorophenyl)-3-(1,1,2,2-tetrafluoroethoxy)propyl]-1H-1,2,4-triazole (EP 234 242);

triadimefon, 1-(4-chlorophenoxy)-3,3-dimethyl-1-(1H-1,2,4-triazol-1-yl)-2-butanone (BE 793 867);

triadimenol, β-(4-chlorophenoxy)-α-(1,1-dimethylethyl)-1H-1,2,4-triazole-1-ethanol (DE 23 24 010);

triflumizol, (4-chloro-2-trifluormethylphenyl)-(2-propoxy-1-[1,2,4]triazol-1-ylethyliden)-amine (JP-A 79/119 462);

triticonazole, (5E)-5-[(4-chlorophenyl)methylene]-2,2-dimethyl-1-(1H-1,2,4-triazol-1-ylmethyl)cyclopentanol (FR 26 41 277);

iprodione, N-isopropyl-3-(3,5-dichlorophenyl)-2,4-dioxoimidazolidine-1-carboxamide (GB 13 12 536);

myclozolin, (RS)-3-(3,5-dichlorophenyl)-5-methoxymethyl-5-methyl-1,3-oxazolidine-2,4-dione [CAS RN 54864-61-8];

procymidone, N-(3,5-dichlorophenyl)-1,2-dimethylcyclopropane-1,2-dicarboximide (U.S. Pat. No. 3,903,090);

vinclozolin, 3-(3,5-dichlorophenyl)-5-methyl-5-vinyloxazolidine-2,4-dione (DE-A 22 07 576);

ferbam, iron(3+) dimethyldithiocarbamate (U.S. Pat. No. 1,972,961);

nabam, disodium ethylenebis(dithiocarbamate) (U.S. Pat. No. 2,317,765);

maneb, manganese ethylenebis(dithiocarbamate) (U.S. Pat. No. 2,504,404);

mancozeb, manganese ethylenebis(dithiocarbamate) polymer complex zinc salt (GB 996 264);

metam, methyldithiocarbaminic acid (U.S. Pat. No. 2,791,605);

metiram, zinc ammoniate ethylenebis(dithiocarbamate) (U.S. Pat. No. 3,248,400);

propineb, zinc propylenebis(dithiocarbamate) polymer (BE 611 960);

polycarbamate, bis(dimethylcarbamodithioato-κ S,κ S')[μ-[[1,2-ethanediylbis[carbamodithioato-κ S,κ S']](2-)]]di[zinc] [CAS RN 64440-88-6];

thiram, bis(dimethylthiocarbamoyl) disulfide (DE 642 532);

ziram, dimethyldithiocarbamate [CAS RN 137-30-4];

zineb, zinc ethylenebis(dithiocarbamate) (U.S. Pat. No. 2,457,674);

anilazine, 4,6-dichloro-N-(2-chlorophenyl)-1,3,5-triazine-2-amine (U.S. Pat. No. 2,720,480);

benomyl, N-butyl-2-acetylaminobenzoimidazole-1-carboxamide (U.S. Pat. No. 3,631,176);

boscalid, 2-chloro-N-(4'-chlorobiphenyl-2-yl)nicotinamide (EP-A 545 099);

carbendazim, methyl (1H-benzoimidazol-2-yl)carbamate (U.S. Pat. No. 3,657,443);

carboxin, 5,6-dihydro-2-methyl-N-phenyl-1,4-oxathiin-3-carboxamide (U.S. Pat. No. 3,249,499);

oxycarboxin, 5,6-dihydro-2-methyl-1,4-oxathiin-3-carboxanilide 4,4-dioxide (U.S. Pat. No. 3,399,214);

cyazofamid, 4-chloro-2-cyano-N,N-dimethyl-5-(4-methylphenyl)-1H-imidazole-1-sulfon-amide [CAS RN 120116-88-3];

dazomet, 3,5-dimethyl-1,3,5-thiadiazinane-2-thione (Bull. Soc. Chim. Fr. Vol. 15, p. 891 (1897));

dithianon, 5,10-dioxo-5,10-dihydronaphtho[2,3-b][1,4]dithiin-2,3-dicarbonitrile (GB 857 383);

famoxadone, (RS)-3-anilino-5-methyl-5-(4-phenoxyphenyl)-1,3-oxazolidine-2,4-dione [CAS RN 131807-57-3];

fenamidone, (S)-1-anilino-4-methyl-2-methylthio-4-phenylimidazolin-5-one [CAS RN 161326-34-7];

fenarimol, α-(2-chlorophenyl)-α-(4-chlorophenyl)-5-pyrimidinemethanol (GB 12 18 623);

fuberidazole, 2-(2-furanyl)-1H-benzimidazole (DE 12 09 799);

flutolanil, α,α,α-trifluoro-3'-isopropoxy-o-toluanilide (JP 1104514);

furametpyr, 5-chloro-N-(1,3-dihydro-1,1,3-trimethyl-4-isobenzofuranyl)-1,3-dimethyl-1H-pyrazole-4-carboxamide [CAS RN 123572-88-3];

isoprothiolane, diisopropyl 1,3-dithiolan-2-ylidenemalonate (Proc. Insectic. Fungic. Conf. 8. Vol. 2, p. 715 (1975));

mepronil, 3'-isopropoxy-o-toluanilide (U.S. Pat. No. 3,937,840);

nuarimol, α-(2-chlorophenyl)-α-(4-fluorophenyl)-5-pyrimidinemethanol (GB 12 18 623);

fluopicolide (picobenzamid), 2,6-dichloro-N-(3-chloro-5-trifluoromethylpyridin-2-ylmethyl)benzamide (WO 99/42447);

probenazole, 3-allyloxy-1,2-benzothiazole 1,1-dioxide (Agric. Biol. Chem. Vol. 37, p. 737 (1973));

proquinazid, 6-iodo-2-propoxy-3-propylquinazolin-4(3H)-one (WO 97/48684);

pyrifenox, 2',4'-dichloro-2-(3-pyridyl)acetophenone (EZ)-O-methyloxime (EP 49 854);

pyroquilon, 1,2,5,6-tetrahydropyrrolo[3,2,1-ij]quinolin-4-one (GB 139 43 373) quinoxyfen, 5,7-dichloro-4-(4-fluorophenoxy)quinoline (U.S. Pat. No. 5,240,940);

silthiofam, N-allyl-4,5-dimethyl-2-(trimethylsilyl)thiophene-3-carboxamide [CAS RN 175217-20-6];

thiabendazole, 2-(1,3-thiazol-4-yl)benzimidazole (U.S. Pat. No. 3,017,415);

thifluzamide, 2',6'-dibromo-2-methyl-4'-trifluoromethoxy-4-trifluormethyl-1,3-thiazole-5-carboxanilide [CAS RN 130000-40-7];

thiophanate-methyl, 1,2-phenylenebis(iminocarbonothioyl)bis(dimethylcarbamate) (DE-A 19 30 540);

tiadinil, 3'-chloro-4,4'-dimethyl-1,2,3-thiadiazole-5-carboxanilide [CAS RN 223580-51-6];

tricyclazole, 5-methyl-1,2,4-triazolo[3,4-b][1,3]benzothiazole [CAS RN 41814-78-2];

triforine, N,N'-{piperazine-1,4-diylbis[(trichlormethyl)methylene]}diformamide (DE 19 01 421);

Bordeaux mixture, mixture of $CuSO_4 \times 3Cu(OH)_2 \times 3CaSO_4$ [CAS RN 8011-63-0] copper acetate, $Cu(OCOCH_3)_2$ [CAS RN 8011-63-0];

copper oxychloride, $Cu_2Cl(OH)_3$ [CAS RN 1332-40-7];

basic copper sulfate, $CuSO_4$ [CAS RN 1344-73-6];

binapacryl, (RS)-2-sec-butyl-4,6-dinitrophenyl 3-methylcrotonate [CAS RN 485-31-4];

dinocap, the mixture of 2,6-dinitro-4-octylphenylcrotonate and 2,4-dinitro-6-octyl-phenylcrotonate, where "octyl" is a mixture of 1-methylheptyl, 1-ethylhexyl and 1-propylpentyl (U.S. Pat. No. 2,526,660);

dinobuton, (RS)-2-sec-butyl-4,6-dinitrophenyl isopropyl carbonate [CAS RN 973-21-7];

nitrothal-isopropyl, diisopropyl 5-nitroisophthalate (Proc. Br. Insectic. Fungic. Conf. 7, Vol. 2, p. 673 (1973));

fenpiclonil, 4-(2,3-dichlorophenyl)-1H-pyrrole-3-carbonitrile (Proc. 1988 Br. Crop Prot. Conf.—Pests Dis., Vol. 1, p. 65);

fludioxonil, 4-(2,2-difluorobenzo[1,3]dioxol-4-yl)-1H-pyrrole-3-carbonitrile (The Pesticide Manual, publ. The British Crop Protection Council, 10th ed. (1995), p. 482);

acibenzolar-S-methyl, methyl 1,2,3-benzothiadiazol-7-carbothioate [CAS RN 135158-54-2];

flubenthiavalicarb (benthiavalicarb), isopropyl {(S)-1-[(1R)-1-(6-fluorobenzothiazol-2-yl)-ethylcarbamoyl]-2-methylpropyl}carbamate (JP-A 09/323,984);

carpropamid, 2,2-dichloro-N-[1-(4-chlorphenyl)ethyl]-1-ethyl-3-methylcyclopropane-carboxamide [CAS RN 104030-54-8];

chlorothalonil, 2,4,5,6-tetrachloroisophthalonitrile (U.S. Pat. No. 3,290,353);

cyflufenamid, (Z)-N-[α-(cyclopropylmethoxyimino)-2,3-difluoro-6-(trifluoromethyl)benzyl]-2-phenylacetamide (WO 96/19442);

cymoxanil, 1-(2-cyano-2-methoxyiminoacetyl)-3-ethylurea (U.S. Pat. No. 3,957,847);

diclomezine, 6-(3,5-dichlorophenyl-p-tolyl)pyridazin-3 (2H)-one (U.S. Pat. No. 4,052,395) diclocymet, (RS)-2-cyano-N—[(R)-1-(2,4-dichlorophenyl)ethyl]-3,3-dimethylbutyramide [CAS RN 139920-32-4];

diethofencarb, isopropyl 3,4-diethoxycarbanilate (EP 78 663); edifenphos, O-ethyl S,S-diphenyl phosphorodithioate (DE 14 93 736) ethaboxam, N-(cyano-2-thienylmethyl)-4-ethyl-2-(ethylamino)-5-thiazolecarboxamide (EP-A 639 574);

fenhexamid, N-(2,3-dichloro-4-hydroxyphenyl)-1-methyl-cyclohexanecarboxamide (Proc. Br. Crop Prot. Conf.—Pests Dis., 1998, Vol. 2, p. 327);

fentin acetate, triphenyltin (U.S. Pat. No. 3,499,086); fenoxanil, N-(1-cyano-1,2-dimethylpropyl)-2-(2,4-dichlorophenoxy)propanamide (EP 262 393);

ferimzone, (Z)-2'-methylacetophenone-4,6-dimethylpyrimidin-2-ylhydrazone [CAS RN 89269-64-7];

fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474);

fosetyl, fosetyl-aluminum, ethylphosphonate (FR 22 54 276);

iprovalicarb, isopropyl [(1S)-2-methyl-1-(1-p-tolylethylcarbamoyl)propyl]carbamate (EP-A 472 996);

hexachlorbenzene (C. R. Seances Acad. Agric. Fr., Vol. 31, p. 24 (1945));

metrafenon, 3'-bromo-2,3,4,6'-tetramethoxy-2',6-dimethylbenzophenone (U.S. Pat. No. 5,945,567);

pencycuron, 1-(4-chlorobenzyl)-1-cyclopentyl-3-phenylurea (DE 27 32 257);

penthiopyrad, (RS)—N-[2-(1,3-dimethylbutyl)-3-thienyl]-1-methyl-3-(trifluoromethyl)-1H-pyrazole-4-carboxamide (JP 10130268);

propamocarb, propyl 3-(dimethylamino)propylcarbamate (DE 15 67 169);

phthalide (DE 16 43 347);

toloclofos-methyl, O-2,6-dichloro-p-tolyl-O,O-dimethyl phosphorothioate (GB 14 67 561);

quintozene, pentachlornitrobenzene (DE 682 048);

zoxamide, (RS)-3,5-dichloro-N-(3-chloro-1-ethyl-1-methyl-2-oxopropyl)-p-toluamide [CAS RN 156052-68-5];

azoxystrobin, methyl 2-{2-[6-(2-cyano-1-vinylpenta-1,3-dienyloxy)pyrimidin-4-yloxy]phenyl}-3-methoxyacrylate (EP 382 375), dimoxystrobin, (E)-2-(methoxyimino)-N-methyl-2-[α-(2,5-xylyloxy)-o-tolyl]acetamide (EP 477 631);

enestroburin, methyl 2-{2-[3-(4-chlorophenyl)-1-methylallylideneaminooxymethyl]-phenyl}-3-methoxyacrylate (EP 936 213);

fluoxastrobin, (E)-{2-[6-(2-chlorophenoxy)-5-fluoropyrimidin-4-yloxy]phenyl}(5,6-dihydro-1,4,2-dioxazin-3-yl) methanone O-methyloxime (WO 97/27189);

kresoxim-methyl, methyl (E)-methoxyimino[α-(o-tolyloxy)-o-tolyl]acetate (EP 253 213);

metominostrobin, (E)-2-(methoxyimino)-N-methyl-2-(2-phenoxyphenyl)acetamide (EP 398 692);

orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552);

picoxystrobin, methyl 3-methoxy-2-[2-(6-trifluoromethylpyridin-2-yloxymethyl)phenyl]-acrylate (EP 278 595);

pyraclostrobin, methyl N-{2-[1-(4-chlorophenyl)-1H-pyrazol-3-yloxymethyl]phenyl}(N-methoxy)carbamate (WO 96/01256);

trifloxystrobin, methyl (E)-methoxyimino-{(E)-α-[1-(α,α,α-trifluoro-m-tolypethylidene-aminooxy]-o-tolyl}acetate (EP 460 575);

captafol, N-(1,1,2,2-tetrachloroethylthio)cyclohex-4-ene-1,2-dicarboximide (Phytopathology, Vol. 52, p. 754 (1962));

captan, N-(trichloromethylthio)cyclohex-4-ene-1,2-dicarboximide (U.S. Pat. No. 2,553,770);

dichlofluanid, N-dichlorofluoromethylthio-N',N'-dimethyl-N-phenylsulfamide (DE 11 93 498);

folpet, N-(trichlormethylthio)phthalimide (U.S. Pat. No. 2,553,770);

tolylfluanid, N-dichlorofluoromethylthio-N',N'-dimethyl-N-p-tolylsulfamide (DE 11 93 498);

dimethomorph, 3-(4-chlorophenyl)-3-(3,4-dimethoxyphenyl)-1-morpholin-4-yl-propenone (EP 120 321);

flumetover, 2-(3,4-dimethoxyphenyl)-N-ethyl-α,α,α-trifluoro-N-methyl-p-toluamide [AGROW no. 243, 22 (1995)];

flumorph, 3-(4-fluorophenyl)-3-(3,4-dimethoxyphenyl)-1-morpholin-4-ylpropenone (EP 860 438).

Practical agricultural experience has shown that the repeated and exclusive application of an individual active compound in the control of harmful fungi leads in many cases to a rapid selection of those fungus strains which have developed natural or adapted resistance against the active compound in question. Effective control of these fungi with the active compound in question is then no longer possible.

To reduce the risk of the selection of resistant fungus strains, mixtures of different active compounds are nowadays conventionally employed for controlling harmful fungi. By combining active compounds having different mechanisms of action, it is possible to ensure successful control over a relatively long period of time.

It is an object of the present invention to provide, with a view to effective resistance management and effective control of phytopathogenic harmful fungi, at application rates which are as low as possible, compositions which, at a reduced total amount of active compounds applied, have improved activity against the harmful fungi (synergistic mixtures) and a broadened activity spectrum, in particular for certain indications.

We have accordingly found that this object is achieved by the compositions, defined at the outset, comprising boscalid, chlorothalonil and an active compound III. Moreover, we have found that simultaneous, that is joint or separate, application of boscalid, chlorothalonil and at least one compound III or successive application of boscalid, chlorothalonil and at least one of the active compounds III allows better control of harmful fungi than is possible with the individual compounds alone (synergistic mixtures).

Boscalid, chlorothalonil and the active compounds III can be present in different crystal modifications, which may differ in biological activity.

The above-mentioned compositions of boscalid, chlorothalonil and at least one of the active compounds III or the simultaneous, that is joint or separate, use of boscalid, chlorothalonil and at least one of the active compounds III are/is distinguished by excellent activity against a broad spectrum of phytopathogenic fungi, for example from the classes of the Ascomycetes, Basidiomycetes, Deuteromycetes and Peronosporomycetes (syn. Oomycetes), in particular from the classes of the Ascomycetes, Basidiomycetes and Deuteromycetes. Some of them are systemically active and can be used in crop protection as foliar fungicides, as soil fungicides and as fungicides for seed dressing.

The compositions according to the invention are particularly important in the control of a multitude of phytopathogenic fungi on various cultivated plants, such as cereals, for example wheat, rye, barley, triticale, oats or rice; beet, for example sugar beet or fodder beet; fruits, such as pomes, stone fruits or soft fruits, for example apples, pears, plums, peaches, almonds, cherries, strawberries, raspberries, blackberries or goose-berries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, for example conifers; and on the plant propagation material, such as seeds, and the crop material of these plants.

Preferably, compounds I and compositions thereof are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be mentioned. These young plants may also be protected before transplantation by a total or partial treatment by immersion or pouring.

Preferably, treatment of plant propagation materials with compounds I and compositions thereof is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant.

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda).

Genetically modified plants capable to synthesize one or more insecticidal proteins are, for example, described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme). The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Ewinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

The term "protein" as used herein is to be understood as an oligopeptide or polypeptide or molecule made up of polypeptides including expressly also pre-proteins, hybrid proteins, peptides, truncated or otherwise modified proteins including those derived from post-transcriptional modifications such as acylation (e.g. acetylation, the addition of an acetyl group, usually at the N-terminus of the protein), alkylation, the addition of an alkyl group (e.g. addition of ethyl or methyl, usually at lysine or arginine residues) or demethylation, amidation at C-terminus, biotinylation (acylation of conserved lysine residues with a biotin appendage), formylation, γ-carboxylation dependent on Vitamin K, glutamylation (covalent linkage of glutamic acid residues), glycosylation (addition of a glycosyl group to either asparagine, hydroxylysine, serine, or threonine, resulting in a glycoprotein), glycation (nonenzymatic attachment of sugars), glycylation (covalent linkage of one to more glycine residues), covalent attachment of a heme moiety, hydroxylation, iodination, isoprenylation (addition of an isoprenoid group such as farnesol and geranylgeraniol), lipoylation (attachment of a lipoate functionality) including prenylation, GPI anchor formation (e.g. myristoylation, farnesylation and geranylgeranylation), covalent attachment of nucleotides or derivatives thereof including ADP-ribosylation and flavin attachment, oxidation, pegylation, covalent attachment of phosphatidylinositol, phosphopantetheinylation (addition of a 4'-phosphopantetheinyl moiety from coenzyme A), phosphorylation (addition of a phosphate group, usually to serine, tyrosine, threonine or histidine), pyroglutamate formation, racemization of proline, tRNA-mediated addition of amino acids such as arginylation, sulfation (addition of a sulfate group to a tyrosine), selenoylation (co-translational incorporation of selenium in selenoproteins), ISGylation (covalent linkage to the ISG15 protein [Interferon-stimulated Gene 15]), SUMOylation (covalent linkage to the SUMO protein [Small Ubiquitin-related MOdifier]), ubiquitination (covalent linkage to the protein ubiquitin or poly-ubiquitin), citrullination or deimination (conversion of arginine to citrulline), deamidation (conversion of glutamine to glutamic acid or asparagine to aspartic acid), formation of disulfide bridges (covalent linkage of two cysteine amino acids) or proteolytic cleavage (cleavage of a protein at a peptide bond).

The plants or seed treated with the combinations of boscalid, chlorothalonil and at least one of the active compounds III may be wildlife types, plants or seed obtained by breeding and transgenic plants as well as their seed.

The inventive compositions are especially suitable for controlling the following phytopathogenic fungi:

*Alternaria atrans tenuissima*
*Alternaria brassicae*
*Alternaria* spp.
*Ascochyta tritici*
*Blumeria graminis*
*Botrytis cinerea*
*Bremia lactucae*
*Bremia lucinae*
*Calonectria crotalariae*
*Cercospora canescens*
*Cercospora kikuchii*
*Cercospora sojina*
*Cercospora canescens*
*Choanephora infundibulifera*
*Cladosporium herbarum*
*Cochliobolus sativus*
*Cochliobolus sativus*
*Colletotrichum truncatum*
*Corynespora cassiicola*
*Dactuliophora glycines*
*Dematophora necatrix*
*Diaporthe phaseolorum*
*Diaporthe phaseolorum* var. *caulivora*
*Drechslera glycini*
*Epicoccum* spp.
*Erwinia amylovora*
*Erysiphe graminis*
*Frogeye sojina*
*Fusarium solani*
*Fusarium culmorum*
*Fusarium graminearum*

-continued

| |
|---|
| *Gaeumannomyces graminis* |
| *Leptosphaeria nodorum* |
| *Leptosphaerulina trifolii* |
| *Macrophomina phaseolina* |
| *Microdochium nivale* |
| *Microsphaera diffusa* |
| *Mycoleptodiscus terrestris* |
| *Neocosmospora vasinfecta* |
| *Pellicularia sasakii* |
| *Peronospora brassicae* |
| *Peronospora manshurica* |
| *Peronospora brassicae* |
| *Peronospora pisi* |
| *Phakopsora pachyrhizi* |
| *Phakopsora meibomiae* |
| *Phialophora gregata* |
| *Phomopsis phaseoli* |
| *Phyllostica sojaecola* |
| *Physiological leaf spots* |
| *Phythium ultimum* |
| *Phytophthora megasperma* |
| *Phytophthora infestans* |
| *Phytopthora megasperma* |
| *Plasmopara viticola* |
| *Podosphaera leucotricha* |
| *Podosphaera leucotricha* |
| *Pseudocercospora herpotrichoides* |
| *Pseudomonas lachrymans* |
| *Pseudomonas syringae* |
| *Pseudoperonospora cubensis* |
| *Pseudoperonospora humuli* |
| *Puccinia hordei* |
| *Puccinia recondita* |
| *Puccinia striiformis* |
| *Puccinia triticina* |
| *Pyrenochaeta glycines* |
| *Pyrenophora allosuri* |
| *Pyrenophora altermarina* |
| *Pyrenophora avenae* |
| *Pyrenophora bartramiae* |
| *Pyrenophora bondarzevii* |
| *Pyrenophora bromi* |
| *Pyrenophora bryophila* |
| *Pyrenophora buddleiae* |
| *Pyrenophora bupleuri* |
| *Pyrenophora calvertii* |
| *Pyrenophora calvescens* var. *moravica* |
| *Pyrenophora carthanie* |
| *Pyrenophora centranthi* |
| *Pyrenophora cerastii* |
| *Pyrenophora chengii* |
| *Pyrenophora chrysamthemi* |
| *Pyrenophora convohuli* |
| *Pyrenophora coppeyana* |
| *Pyrenophora cytisi* |
| *Pyrenophora dactylidis* |
| *Pyrenophora dictyoides* |
| *Pyrenophora echinopis* |
| *Pyrenophora ephemera* |
| *Pyrenophora eryngicola* |
| *Pyrenophora erythrospila* |
| *Pyrenophora euphorbiae* |
| *Pyrenophora freticola* |
| *Pyrenophora graminea* |
| *Pyrenophora graminea* |
| *Pyrenophora heraclei* |
| *Pyrenophora hordei* |
| *Pyrenophora horrida* |
| *Pyrenophora hyperici* |
| *Pyrenophora japonica* |
| *Pyrenophora kugitangi* |
| *Pyrenophora lithophila* |
| *Pyrenophora lolii* |
| *Pyrenophora macrospora* |
| *Pyrenophora metasequoiae* |
| *Pyrenophora minuertiae hirsutae* |
| *Pyrenophora moravica* |
| *Pyrenophora moroczkowskii* |
| *Pyrenophora muscorum* |
| *Pyrenophora osmanthi* |

-continued

| |
|---|
| *Pyrenophora phlei* |
| *Pyrenophora pimpinellae* |
| *Pyrenophora pittospori* |
| *Pyrenophora polytricha* |
| *Pyrenophora pontresinerisis* |
| *Pyrenophora pulsatillae* |
| *Pyrenophora raetica* |
| *Pyrenophora rayssiae* |
| *Pyrenophora rugosa* |
| *Pyrenophora ryohicola* |
| *Pyrenophora saviczii* |
| *Pyrenophora schoeteri* |
| *Pyrenophora scholevskii* |
| *Pyrenophora scirpi* |
| *Pyrenophora scirpicola* |
| *Pyrenophora secalis* |
| *Pyrenophora semeniperda* |
| *Pyrenophora semiusta* |
| *Pyrenophora seseli* |
| *Pyrenophora seseli* f. *poterii* |
| *Pyrenophora subalpina* |
| *Pyrenophora sudetica* |
| *Pyrenophora suhantarctica* |
| *Pyrenophora syntrichiae* |
| *Pyrenophora szaferiana* |
| *Pyrenophora teres* |
| *Pyrenophora teres* f. *makulata* |
| *Pyrenophora teres* subsp. *graminea* |
| *Pyrenophora tetrahenae* |
| *Pyrenophora tranzschelii* |
| *Pyrenophora trifulii* |
| *Pyrenophora triticil-repentis* |
| *Pyrenophora ushuwaiensis* |
| *Pyrenophora villose* |
| *Pyrenophora graminea* |
| *Pyrenophora teres* |
| *Pyrenophora teres* |
| *Pyrenophora teres* |
| *Pyrenophora tritici repentis* |
| *Pyricularia oryzae* |
| *Pythium aphanidermatum* |
| *Pythium debaryanum* |
| *Pythium irregulare* |
| *Pythium myriotylum* |
| *Pythium ultimum* |
| *Ramularia collocygni* |
| *Rhizoctonia aerea* |
| *Rhizoctonia alba* |
| *Rhizoctonia alpina* |
| *Rhizoctonia anaticula* |
| *Rhizoctonia anomala* |
| *Rhizoctonia apocynacearum* |
| *Rhizoctonia arachnion* |
| *Rhizoctonia asclerotica* |
| *Rhizoctonia batalicola* |
| *Rhizoctonia borealis* |
| *Rhizoctonia callae* |
| *Rhizoctonia carorae* |
| *Rhizoctonia cerealis* |
| *Rhizoctonia choussii* |
| *Rhizoctonia coniothecioides* |
| *Rhizoctonia cundida* |
| *Rhizoctonia dichoroma* |
| *Rhizoctonia dimorpha* |
| *Rhizoctonia endophytica* |
| *Rhizoctonia endophytica* vor. *filicata* |
| *Rhizoctonia ferruginea* |
| *Rhizoctonia floccosa* |
| *Rhizoctonia fragariae* |
| *Rhizoctonia fraxini* |
| *Rhizoctonia fuliginea* |
| *Rhizoctonia fumigata* |
| *Rhizoctonia globularis* |
| *Rhizoctonia goodyerae-repentis* |
| *Rhizoctonia gossypii* |
| *Rhizoctonia gossypii* vor. *anatolica* |
| *Rhizoctonia gracilis* |
| *Rhizoctonia griseo* |
| *Rhizoctonia hiemalis* |
| *Rhizoctonia juniperi* |

*Rhizoctonia lamallifera*
*Rhizoctonia leguminicola*
*Rhizoctonia lilacina*
*Rhizoctonia luoini*
*Rhizoctonia macrosclerotia*
*Rhizoctonia melongenae*
*Rhizoctonia microsclerotia*
*Rhizoctonia monilioides*
*Rhizoctonia monteithiana*
*Rhizoctonia muneratii*
*Rhizoctonia nandorii*
*Rhizoctonia oryzae*
*Rhizoctonia oryzae-sativae*
*Rhizoctonia pallida*
*Rhizoctonia pini-insignis*
*Rhizoctonia praticola*
*Rhizoctonia quercus*
*Rhizoctonia ramicola*
*Rhizoctonia robusta*
*Rhizoctonia rubi*
*Rhizoctonia ruhiginosa*
*Rhizoctonia sclerotica*
*Rhizoctonia solani*
*Rhizoctonia solani* f. *paroketea*
*Rhizoctonia solani forma specialis*
*Rhizoctonia solani* var. *cedri-deodorae*
*Rhizoctonia solani* var. *fuchsiae*
*Rhizoctonia solani* var. *hortensis*
*Rhizoctonia stahlii*
*Rhizoctonia subtilis* var. *nigra*
*Rhizoctonia subtlilis*
*Rhizoctonia tomato*
*Rhizoctonia tuliparum*
*Rhizoctonia veae*
*Rhizoctonia versicolor*
*Rhizoctonia cerealis*
*Rhynchosporium secalis*
*Sclerotina rolfsii*
*Sclerotinia rolfsii*
*Sclerotinia sclerotiorum*
*Septoria glycines*
*Septoria nodorum*
*Septoria tritici*
*Sphaerotheca fuliginea*
*Stagonospora nodorum*
*Stemphylium botryosum*
*Thielaviopsis basicola*
*Tilletia aegilopis*
*Tilletia aegopogonis*
*Tilletia ahamadiana*
*Tilletia airina*
*Tilletia ajrekari*
*Tilletia alopecuri*
*Tilletia anthaxanthi*
*Tilletia apludae*
*Tilletia armdinellae*
*Tilletia asperifolia*
*Tilletia asperitolioides*
*Tilletia atacamensis*
*Tilletia baldrati*
*Tilletia bambusae*
*Tilletia banarasae*
*Tilletia bangalorensis*
*Tilletia barclayana*
*Tilletia biharica*
*Tilletia boliviensis*
*Tilletia boutelouae*
*Tilletia brachypodii*
*Tilletia brachypodii-ramosi*
*Tilletia braomi-tectorum*
*Tilletia brevifaciens*
*Tilletia bromi*
*Tilletia bromina*
*Tilletia brunkii*
*Tilletia buchloeana*
*Tilletia bulayi*
*Tilletia caries*
*Tilletia cathcariae*
*Tilletia cerebrina*
*Tilletia chloridicola*
*Tilletia contaoversa*
*Tilletia contraversa* var. *prostrata*
*Tilletia contraversa* var. *elyni*
*Tilletia corona*
*Tilletia cynasuri*
*Tilletia damacarae*
*Tilletia deyeuxiae*
*Tilletia digitariicola*
*Tilletia durangensis*
*Tilletia earlei*
*Tilletia echinochlave*
*Tilletia echinochloae*
*Tilletia echinosperma*
*Tilletia ehrhartae*
*Tilletia eleusines*
*Tilletia elymandrae*
*Tilletia elymicola*
*Tilletia elyni*
*Tilletia elythrophori*
*Tilletia eragrostidis*
*Tilletia euphorbiae*
*Tilletia fahrendorfii*
*Tilletia festinca-octoflorana*
*Tilletia foelida*
*Tilletia foliicola*
*Tilletia fusca*
*Tilletia fusca* var. *bromi-tectorum*
*Tilletia fusca* var. *guyotiana*
*Tilletia fusca* var. *paragonica*
*Tilletia georfischeri*
*Tilletia gigaspora*
*Tilletia goloskokovii*
*Tilletia haynaldiae*
*Tilletia heterospora*
*Tilletia holci*
*Tilletia hordei* var. *spontanei*
*Tilletia horrida*
*Tilletia hyalospora* var. *cuzcoensis*
*Tilletia hyparrheniae*
*Tilletia indica*
*Tilletia iniermedia*
*Tilletia iovensis*
*Tilletia ixophari*
*Tilletia koeleriae*
*Tilletia kuznetzoviana*
*Tilletia laevis*
*Tilletia laguri*
*Tilletia leptochlase*
*Tilletia lepturi*
*Tilletia macrotuberculata*
*Tilletia madeirensis*
*Tilletia maglagonii*
*Tilletia makutensis*
*Tilletia milti*
*Tilletia milti-vernalis*
*Tilletia montana*
*Tilletia montemartinii*
*Tilletia nanifica*
*Tilletia narasimhanii*
*Tilletia narayanaoana*
*Tilletia narduri*
*Tilletia nigrifaciens*
*Tilletia obscura-reticulora*
*Tilletia oklahomae*
*Tilletia okudoirae*
*Tilletia oplistneni-cristati*
*Tilletia paae*
*Tilletia pachyderma*
*Tilletia pallida*
*Tilletia panici*
*Tilletia panici.* *humilis*
*Tilletia paonensis*
*Tilletia paraloxa*
*Tilletia paspali*
*Tilletia pennisetina*
*Tilletia peritidis*
*Tilletia phalaridis*
*Tilletia polypoganis*
*Tilletia prostrata*
*Tilletia pulcherrima* var. *brachiariae*

-continued

*Tilletia redfieldiae*
*Tilletia rhei*
*Tilletia rugispora*
*Tilletia sabaudiae*
*Tilletia salzmanii*
*Tilletia savilei*
*Tilletia scrobiculata*
*Tilletia setariae*
*Tilletia setariae-palmiflorarae*
*Tilletia setariicola*
*Tilletia sphaerococca*
*Tilletia sphenopie*
*Tilletia sphenopodis*
*Tilletia sterilis*
*Tilletia taiana*
*Tilletia texana*
*Tilletia themedae-anatherae*
*Tilletia themedicola*
*Tilletia toguateei*
*Tilletia trachypogonis*
*Tilletia transiliensis*
*Tilletia transvaalensis*
*Tilletia tritici* f. *monococci*
*Tilletia tritici* var. *controversa*
*Tilletia tritici* var. *nanifica*
*Tilletia tritici* var. *laevis*
*Tilletia tritici-repentis*
*Tilletia triticoides*
*Tilletia tuberculare*
*Tilletia vertiveriae*
*Tilletia viermotii*
*Tilletia vittara*
*Tilletia vittara* var. burmahnii
*Tilletia walkeri*
*Tilletia youngii*
*Tilletia zundelii*
*Typhula incarnata*
*Uromyces appendiculatus*
*Ustilago aaeluropodis*
*Ustilago abstrusa*
*Ustilago aegilopsidis*
*Ustilago affinis* var. *hilariae*
*Ustilago agrestis*
*Ustilago agropyrina*
*Ustilago agrostis-palustris*
*Ustilago airear-caespitosae*
*Ustilago alismatis*
*Ustilago almadina*
*Ustilago alopecurivara*
*Ustilago alsineae*
*Ustilago altilis*
*Ustilago amadelpha* var. *glabriuscula*
*Ustilago amphilophidis*
*Ustilago amplexa*
*Ustilago amthoxanthi*
*Ustilago andropogonis-tectorum*
*Ustilago aneilemae*
*Ustilago anhweiona*
*Ustilago anomala* var. *avicularis*
*Ustilago anomala* var. *carnea*
*Ustilago anomala* var. *cordai*
*Ustilago anomala* var. *microspora*
*Ustilago anomala* var. *muricata*
*Ustilago anomala* var. *tovarae*
*Ustilago apscheronica*
*Ustilago arabidia.alpinae*
*Ustilago arandinellae-hirtae*
*Ustilago arctica*
*Ustilago argentina*
*Ustilago aristidarius*
*Ustilago arotragostis*
*Ustilago asparagi-pygmaei*
*Ustilago asprellae*
*Ustilago avanae* subsp. *alba*
*Ustilago avenae*
*Ustilago avenae*
*Ustilago avenae* f. sp. *perennars*
*Ustilago avenariae-bryophyllae*
*Ustilago avicularis*
*Ustilago bahuichivoensis*

-continued

*Ustilago barbari*
*Ustilago beckeropsis*
*Ustilago belgiana*
*Ustilago bethelii*
*Ustilago bicolor*
*Ustilago bistortarum ustiloginea*
*Ustilago bistortarum* var. *pustulata*
*Ustilago boreatis*
*Ustilago bothriochloae*
*Ustilago bothriochloae-intermediae*
*Ustilago bouriqueti*
*Ustilago braziliensis*
*Ustilago brisae*
*Ustilago bromi-arvensis*
*Ustilago bromi-erecti*
*Ustilago bromi-mallis*
*Ustilago bromina*
*Ustilago bromivora* f. *brachypodii*
*Ustilago bromivora* var. *microspora*
*Ustilago bullata* f. *brachypodii-distachyi*
*Ustilago bullata* var. *bonariesis*
*Ustilago bullata* var. *macrospora*
*Ustilago bungeana*
*Ustilago calanagrostidis*
*Ustilago calanagrostidis* var. *scrobiculata*
*Ustilago calanagrostidis* var. *typica*
*Ustilago cardamines*
*Ustilago cariciphila*
*Ustilago caricis-wallichianae*
*Ustilago carnea*
*Ustilago catherimae*
*Ustilago caulicola*
*Ustilago cenrtodomis*
*Ustilago ceparum*
*Ustilago cephalariae*
*Ustilago chacoensis*
*Ustilago chloridii*
*Ustilago chloridionis*
*Ustilago chrysopoganis*
*Ustilago chubulensis*
*Ustilago cichorii*
*Ustilago cilmodis*
*Ustilago clelandii*
*Ustilago clintoniana*
*Ustilago coloradensis*
*Ustilago commelinae*
*Ustilago compacta*
*Ustilago concelata*
*Ustilago condigna*
*Ustilago consimilis*
*Ustilago constantineanui*
*Ustilago controversa*
*Ustilago conventere-sexualis*
*Ustilago cordai*
*Ustilago corlarderiae* var. *araucana*
*Ustilago coronariaw*
*Ustilago coronata*
*Ustilago courtoisii*
*Ustilago crus-galli* var. *minor*
*Ustilago cryptica*
*Ustilago curta*
*Ustilago custanaica*
*Ustilago cynodontis*
*Ustilago cynodontis*
*Ustilago cyperi-lucidi*
*Ustilago davisii*
*Ustilago deccanii*
*Ustilago decipiens*
*Ustilago deformitis*
*Ustilago dehiscens*
*Ustilago delicata*
*Ustilago deyeuxiae*
*Ustilago dianthorum*
*Ustilago distichlidis*
*Ustilago dubiosa*
*Ustilago dumosa*
*Ustilago earlei*
*Ustilago echinochloae*
*Ustilago ehrhartana*
*Ustilago eleocharidis*

-continued

*Ustilago eleusines*
*Ustilago elymicola*
*Ustilago elytrigiae*
*Ustilago enneapogonis*
*Ustilago epicampida*
*Ustilago eragrostidis-japanicana*
*Ustilago eriocauli*
*Ustilago eriochloae*
*Ustilago euphorbiae*
*Ustilago fagopyri*
*Ustilago festucae*
*Ustilago festucorum*
*Ustilago filamenticola*
*Ustilago fingerhuthiae*
*Ustilago flectens*
*Ustilago flonersii*
*Ustilago foliorum*
*Ustilago formosana*
*Ustilago fueguina*
*Ustilago gageae*
*Ustilago garcesi*
*Ustilago gardneri*
*Ustilago gausenii*
*Ustilago gayazana*
*Ustilago gigantispora*
*Ustilago glyceriae*
*Ustilago gregaria*
*Ustilago grossheimii*
*Ustilago gunnerae*
*Ustilago haesendocki* var. *chloraphorae*
*Ustilago haesendocki* var. *vargasii*
*Ustilago halophiloides*
*Ustilago haynalodiae*
*Ustilago heleochloae*
*Ustilago helictotrichi*
*Ustilago herteri* var. *Bicolor*
*Ustilago herteri* var. *vargasii*
*Ustilago hierochloae-adoratae*
*Ustilago hieronymi* var. *insularis*
*Ustilago hieronymi* var. *minor*
*Ustilago hilariicola*
*Ustilago hilubii*
*Ustilago himalensis*
*Ustilago histortarum* var. *marginalis*
*Ustilago hitchcockiana*
*Ustilago holci-avanacei*
*Ustilago hordei*
*Ustilago hordei* f. sp. *avenae*
*Ustilago hsuii*
*Ustilago hyalino-bipolaris*
*Ustilago hydropiperis*
*Ustilago hyparrheniae*
*Ustilago hypodyies* f. *congoensis*
*Ustilago hypodytes* f. *sporaboli*
*Ustilago hypodytes* var. *agrestis*
*Ustilago idonea*
*Ustilago imperatue*
*Ustilago induia*
*Ustilago inouyei*
*Ustilago intercedens*
*Ustilago iranica*
*Ustilago isachnes*
*Ustilago ischaemi-akoensis*
*Ustilago ischaemi-anthephoroides*
*Ustilago ixiolirii*
*Ustilago ixophori*
*Ustilago jacksonii*
*Ustilago jacksonii* var. *vintonesis*
*Ustilago jaczevskyana*
*Ustilago jaczevskyana* van. *typica*
*Ustilago jaczevskyana* var. *sibirica*
*Ustilago jagdishwari*
*Ustilago jamalainentii*
*Ustilago jehudana*
*Ustilago johnstonii*
*Ustilago kairamoi*
*Ustilago kasuchstemica*
*Ustilago kenjiana*
*Ustilago kweichowensis*
*Ustilago kylingae*
*Ustilago lacjrymae-jobi*
*Ustilago lepyrodiclidis*
*Ustilago lidii*
*Ustilago liebenbergii*
*Ustilago linderi*
*Ustilago linearis*
*Ustilago lirove*
*Ustilago loliicola*
*Ustilago longiflora*
*Ustilago longiseti*
*Ustilago longissima* var. *dubiosa*
*Ustilago longissima* var. *paludificans*
*Ustilago longissima* var. *typical*
*Ustilago lupini*
*Ustilago lychnidis-dioicae*
*Ustilago lycoperdiformis*
*Ustilago lyginiae*
*Ustilago machili*
*Ustilago machringiae*
*Ustilago magalaspora*
*Ustilago magellanica*
*Ustilago mariscana*
*Ustilago maydis*
*Ustilago melicae*
*Ustilago merxmuellerana*
*Ustilago mesatlantica*
*Ustilago michnoana*
*Ustilago microspora*
*Ustilago microspora* var. *paspalicola*
*Ustilago microstegii*
*Ustilago microthelis*
*Ustilago milli*
*Ustilago mobtagnei* var. *minor*
*Ustilago modesta*
*Ustilago moenchiae-manticae*
*Ustilago monermae*
*Ustilago morinae*
*Ustilago morobiana*
*Ustilago mrucata*
*Ustilago muda*
*Ustilago muehlenbergiae* var. *lucumanensis*
*Ustilago muscaribotryoidis*
*Ustilago nagarnyi*
*Ustilago nannfeldtii*
*Ustilago nauda* var. *hordei*
*Ustilago nelsoniana*
*Ustilago nepalensis*
*Ustilago neyraudiae*
*Ustilago nigra*
*Ustilago nivalis*
*Ustilago nuda*
*Ustilago nuda*
*Ustilago nuda* var. *tritici*
*Ustilago nyassae*
*Ustilago okudairae*
*Ustilago olida*
*Ustilago olivacea* var. *macrospora*
*Ustilago onopordi*
*Ustilago onumae*
*Ustilago opiziicola*
*Ustilago oplismeni*
*Ustilago orientalis*
*Ustilago otophora*
*Ustilago ovariicola*
*Ustilago overcemii*
*Ustilago pamirica*
*Ustilago panici-geminati*
*Ustilago panjabensis*
*Ustilago pappophori*
*Ustilago pappophori* var. *magdalensis*
*Ustilago parasnothii*
*Ustilago parodii*
*Ustilago parvula*
*Ustilago paspalidiicola*
*Ustilago patagonica*
*Ustilago penniseti* var. *verruculosa*
*Ustilago perrara*
*Ustilago persicariae*
*Ustilago petrakii*
*Ustilago phalaridis*

*Ustilago phlei*
*Ustilago phlei-protensis*
*Ustilago phragmites*
*Ustilago picacea*
*Ustilago pimprina*
*Ustilago piperi* (var.) *rosulata*
*Ustilago poae*
*Ustilago poae-bulbosae*
*Ustilago poae-nemoralis*
*Ustilago polygoni-alati*
*Ustilago polygoni-alpini*
*Ustilago polygoni-punctari*
*Ustilago polygoni-serrulati*
*Ustilago polytocae*
*Ustilago polytocae-harbatas*
*Ustilago pospelovii*
*Ustilago prostrata*
*Ustilago pseudohieronymi*
*Ustilago puehlaensis*
*Ustilago puellaris*
*Ustilago pulvertulensa*
*Ustilago raciborskiana*
*Ustilago radians*
*Ustilago ravida*
*Ustilago rechingeri*
*Ustilago reticulara*
*Ustilago reticulispora*
*Ustilago rhei*
*Ustilago rhynchelytri*
*Ustilago ruandenis*
*Ustilago ruberculata*
*Ustilago sabouriana*
*Ustilago salviae*
*Ustilago sanctae-catharinae*
*Ustilago scaura*
*Ustilago scillae*
*Ustilago scitaminea*
*Ustilago scitaminea* var. *sacchar-officinorum*
*Ustilago scleranthi*
*Ustilago scrobiculata*
*Ustilago scutulata*
*Ustilago secalis* var. *elymi*
*Ustilago seitaminea* var. *sacchari-barberi*
*Ustilago semenoviana*
*Ustilago serena*
*Ustilago serpens*
*Ustilago sesleriae*
*Ustilago setariae-mambassanae*
*Ustilago shastensis*
*Ustilago shimadae*
*Ustilago silenes-inflatae*
*Ustilago silenes-nutantis*
*Ustilago sinkiangensis*
*Ustilago sitanil*
*Ustilago sleuneri*
*Ustilago sonoriana*
*Ustilago sorghi-stipoidei*
*Ustilago spadicea*
*Ustilago sparoboli-indici*
*Ustilago sparti*
*Ustilago speculariae*
*Ustilago spegazzinii*
*Ustilago spegazzinii* var. *agrestis*
*Ustilago spermophora* var. *orientalis*
*Ustilago spermophoroides*
*Ustilago spinulosa*
*Ustilago sporoboli-trenuli*
*Ustilago stellariae*
*Ustilago sterilis*
*Ustilago stewartli*
*Ustilago stipae*
*Ustilago striaeformis* f. *phlei*
*Ustilago striaeformis* f. *poa* . . .
*Ustilago striaeformis* f. *poae-pratensis*
*Ustilago striiformis* f. *hierochloes-odoratae*
*Ustilago striiformis* var. *agrostidis*
*Ustilago striiformis* var. *dactylidis*
*Ustilago striiformis* var. *holci*
*Ustilago striiformis* var. *phlei*
*Ustilago striiformis* var. *poae*
*Ustilago sumnevicziana*
*Ustilago superha*
*Ustilago sydowiana*
*Ustilago symbiotica*
*Ustilago taenia*
*Ustilago taiana*
*Ustilago tanakue*
*Ustilago tenuispora*
*Ustilago thaxteri*
*Ustilago tinontiae*
*Ustilago togata*
*Ustilago tournenxii*
*Ustilago tovarae*
*Ustilago trachophora* var. *pacifica*
*Ustilago trachyniae*
*Ustilago trachypogonis*
*Ustilago tragana*
*Ustilago tragi*
*Ustilago tragica*
*Ustilago tragi-racemosi*
*Ustilago trichoneurana*
*Ustilago trichophora* var. *crus-galli*
*Ustilago trichophora* var. *panici-frumentacei*
*Ustilago triseti*
*Ustilago tritici forma specialis*
*Ustilago tucumariensis*
*Ustilago tumeformis*
*Ustilago turcomanica*
*Ustilago turcomanica* var. *prostrata*
*Ustilago turcomanica* var. *typica*
*Ustilago ugamica*
*Ustilago ugandensis* var. *macrospora*
*Ustilago underwoodii*
*Ustilago urginede*
*Ustilago urochloana*
*Ustilago ustilaginea*
*Ustilago ustriculosa* var. *cordai*
*Ustilago ustriculosa* var. *reticulata*
*Ustilago valentula*
*Ustilago vavilori*
*Ustilago verecunda*
*Ustilago verruculosa*
*Ustilago versatilis*
*Ustilago vetiveriae*
*Ustilago violaceo-irregularis*
*Ustilago violaceu* var. *stellariae*
*Ustilago violaceuverrucosa*
*Ustilago williamsii*
*Ustilago wynaadensis*
*Ustilago zambettakisii*
*Ustilago zernae*
*Venturia inaequalis*
*Xanthomonas campestris*
*Xanthomonas oryzae*

The inventive compositions are particularly suitable for controlling phytopathogenic fungi in barley and wheat (e.g. *Blumeria graminis, Fusarium culmorum, Gaeumannomyces graminis, Microdochium nivale, Pseudocercosporella herpotrichoides, Puccinia hordei, Puccinia recondita, Puccinia striiformis, Pyrenophora teres, Ramularia collo-cygni*/Physiological leaf spots, *Rhizoctonia cerealis, Rhynchosporium secalis, Septoria nodorum, Septoria tritici, Typhula incarnata*) and soybeans (e.g. *Alternaria* spp., *Cercospora sojina, Cercospora kikuchii, Corynespora cassiicola, Colletotrichum truncatum, Dematophora necatrix, Diaporthe phaseolorum, Fusarium solani, Macrophomina phaseolina, Microsphaera diffusa, Phakopsora pachyrhizi, Peronospora manshurica, Phomopsis phaseoli, Phialophora gregata, Phytopthora megasperma, Rhizoctonia solani, Septoria glycines, Sclerotinia rolfsii, Sclerotinia sclerotiorum*).

The inventive compositions are particularly suitable for controlling phytopathogenic fungi in barley as mentioned above. Particularly, they exhibit an excellent activity against *Ramularia collo-cygni*/Physiological leaf spots.

The compositions according to the invention are furthermore suitable for controlling harmful fungi in the protection of materials (for example wood, paper, paint dispersions, fibers or fabrics) and in the protection of stored products. In the protection of wood, particular attention is paid to the following harmful fungi: *Ascomycetes*, such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; *Basidiomycetes*, such as *Coniophora* spp., *Coriolus* spp., *Gloeophyllum* spp., *Lentinus* spp., *Pleurotus* spp., *Poria* spp., *Serpula* spp. and *Tyromyces* spp., *Deuteromycetes*, such as *Aspergillus* spp., *Cladosporium* spp., *Penicillium* spp., *Trichoderma* spp., *Alternaria* spp., *Paecilomyces* spp. and *Zygomycetes*, such as *Mucor* spp., additionally in the protection of materials the following yeasts: *Candida* spp. and *Saccharomyces cerevisae*.

Application of the inventive compositions to useful plants may also lead to an increase in the crop yield.

Boscalid, chlorothalonil and at least one of the active compounds III can be applied simultaneously, that is jointly or separately, or in succession, the sequence, in the case of separate application, generally not having any effect on the result of the control measures.

When preparing the compositions, it is preferred to employ the pure active compounds, to which further compounds active against harmful fungi or other pests, such as insects, arachnids or nematodes, or else herbicidal or growth-regulating active compounds or fertilizers can be added.

Preference is given to compositions comprising boscalid, chlorothalonil and at least one active compound selected from the groups A), B), C), D) and E), in particular A), B), D) and E), most preferably group A).

Particular preference is given to compositions comprising boscalid, chlorothalonil and epoxyconazole, fluquinconazole, metconazole, tebuconazole or triticonazole. Very particularly preferred are compositions comprising boscalid, chlorothalonil and epoxyconazole, metconazole, tebuconazole or triticonazole, in particular epoxyconazole or metconazole.

In one embodiment of the compositions according to the invention, a further fungicide (V) is added to the compositions comprising boscalid, chlorothalonil and a fungicidally active compound III.

Suitable further fungicides (V) are the active compounds III mentioned above.

Compositions comprising boscalid, chlorothalonil and one component III are preferred.

Boscalid, chlorothalonil and the compounds III are usually applied in a weight ratio of from 100:1:5 to 1:100:20, preferably from 20:1:1 to 1:20:20 to 1:20:1 to 20:1:20, in particular from 10:1:1 to 1:10:10 to 1:10:1 to 10:1:10.

The components V are, if desired, added in a ratio of from 20:1 to 1:20 to the compositions comprising boscalid, chlorothalonil and an active compound III.

Depending on the type of compound(s) III and the desired effect, the application rates of the mixtures according to the invention are from 5 g/ha to 2500 g/ha, preferably from 5 g/ha to 1000 g/ha, in particular from 50 to 750 g/ha.

Correspondingly, the application rates for boscalid are generally from 1 to 1000 g/ha, preferably from 10 to 900 g/ha, in particular from 20 to 750 g/ha.

Correspondingly, the application rates for chlorothalonil are generally from 1 to 1000 g/ha, preferably from 10 to 500 g/ha, in particular from 40 to 350 g/ha.

Correspondingly, the application rates for the active compounds III are generally from 1 to 1000 g/ha, preferably from 10 to 500 g/ha, in particular from 40 to 350 g/ha.

In the treatment of seed, application rates of the inventive compositions are generally from 1 to 1000 g/100 kg of seed, preferably from 1 to 200 g/100 kg, in particular from 5 to 100 g/100 kg.

The method for controlling harmful fungi is carried out by the separate or joint application of boscalid, chlorothalonil and a compound III or of the compositions comprising boscalid, chlorothalonil and a compound III, by spraying or dusting the seeds, the plants or the soil before or after sowing of the plants or before or after emergence of the plants.

The compositions according to the invention, or boscalid, chlorothalonil and the compounds III separately, can be converted into customary formulations (agents), for example solutions, emulsions, suspensions, dusts, powders, pastes and granules. The use form depends on the particular intended purpose; in each case, it should ensure a fine and even distribution of the respective compound(s) according to the invention.

The formulations are prepared in a known manner, for example by extending the active compound(s) with at least one solvent and/or carrier, if desired using emulsifiers and dispersants. Solvents/auxiliaries suitable for this purpose are essentially:

water, aromatic solvents (for example Solvesso® products, xylene), paraffins (for example mineral oil fractions), alcohols (for example methanol, butanol, pentanol, benzyl alcohol), ketones (for example cyclohexanone, gamma-butyrolactone), pyrrolidones (N-methylpyrrolidone, N-octylpyrrolidone), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalene-] sulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compound(s) to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compounds( ). The active compound(s) are generally employed in a purity of from 90% to 100%, preferably 95% to 100% (according to NMR spectrum).

The following are examples of formulations: 1. Products for dilution with water
A) Water-Soluble Concentrates (SL)
  10 parts by weight of active compound(s) are dissolved in 90 parts by weight of water or in a water-soluble solvent. As an alternative, wetting agents or other auxiliaries are added. The active compound dissolves upon dilution with water. In this way, a formulation having a content of 10% by weight of active compound(s) is obtained.
B) Dispersible Concentrates (DC)
  20 parts by weight of active compound(s) are dissolved in 70 parts by weight of cyclohexanone with addition of 10 parts by weight of a dispersant, for example polyvinylpyrrolidone. Dilution with water gives a dispersion. The active compound content is 20% by weight.
C) Emulsifiable Concentrates (EC)
  15 parts by weight of active compound(s) are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.
D) Emulsions (EW, EO)
  25 parts by weight of active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The formulation has an active compound content of 25% by weight.
E) Suspensions (SC, OD)
  In an agitated ball mill, 20 parts by weight of active compound(s) are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.
F) Water-Dispersible Granules and Water-Soluble Granules (WG, SG)
  50 parts by weight of active compound(s) are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.
G) Water-Dispersible Powders and Water-Soluable Powders (WP, SP)
  75 parts by weight of active compound(s) are ground in a rotor-stator mill with addition of 25 parts by weight of dispersants, wetting agents and silica gel. Dilution with water gives a stable dispersion or solution of the active compound. The active compound content of the formulation is 75% by weight.
2. Products to be Applied Undiluted
H) Dustable Powders (DP)
  5 parts by weight of active compound(s) are ground finely and mixed intimately with 95 parts by weight of finely divided kaolin. This gives a dustable product having an active compound content of 5% by weight.
J) Granules (GR, FG, GG, MG)
  0.5 part by weight of active compound(s) are ground finely and associated with 99.5 parts by weight of carriers. Current methods are extrusion, spray-drying or the fluidized bed. This gives granules to be applied undiluted having an active compound content of 0.5% by weight.
K) ULV Solutions (UL)
  10 parts by weight of active compound(s) are dissolved in 90 parts by weight of an organic solvent, for example xylene. This gives a product to be applied undiluted having an active compound content of 10% by weight.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetting agent, tackifier, dispersant or emulsifier. However, it is also possible to prepare concentrates composed of active substance, wetting agent, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), it being possible to apply formulations comprising over 95% by weight of active compound, or even to apply the active compound without additives.

Oils of various types, wetting agents or adjuvants may be added to the active compounds, even, if appropriate, not until immediately prior to use (tank mix). These agents are typically admixed with the compositions according to the invention in a weight ratio of from 1:100 to 100:1, preferably from 1:10 to 10:1.

Suitable adjuvants in this sense are in particular: organically modified polysiloxanes, for example BREAK THRU S 240®; alcohol alkoxylates, for example ATPLUS 245®, ATPLUS MBA 1303®, PLURAFAC LF 300® and LUTENSOL ON 30®; EO/PO block polymers, for example PLURONIC RPE 2035® and GENAPOL B®; alcohol ethoxylates, for example LUTENSOL XP 80®; and sodium dioctylsulfosuccinate, for example LEOPHEN RA®.

Boscalid, chlorothalonil and the compounds III or the compositions or the corresponding agents (formulations) applied by treating the harmful fungi, the plants, seeds, soils, areas, materials or spaces to be kept free from them with a fungicidally effective amount of the composition or, in the case of separate application, of boscalid, chlorothalonil and compound III, respectively. Application can be before or after the infection by harmful fungi.

The fungicidal action of the individual compounds and of the compositions according to the invention was demonstrated by the tests below.

The active compounds were formulated separately as a stock solution having a concentration of 10000 ppm in dimethylsulfoxide. Boscalid, epoxiconazole, trifloxystrobin and benthiavalicarb were used as commercial finished formulations and diluted with water to the stated concentrations of the respective active compound.

The measured parameters were compared to the growth of the active compound-free control variant (100%) and the fungus-free and active compound-free blank value to determine the relative growth in % of the pathogens in the respective active compounds. These percentages were converted into efficacies.

An efficacy of 0 means that the growth level of the pathogens corresponds to that of the untreated control; an efficacy of 100 means that the pathogens were not growing.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

Colby's formula: $E = x + y - x \cdot y / 100$

E expected efficacy, expressed in % of the untreated control, when using the mixture of the active compounds A and B at the concentrations a and b x efficacy, expressed in % of the untreated control, when using the active compound A at the concentration a y efficacy, expressed in % of the untreated control, when using the active compound B at the concentration b The test results show that, by virtue of the strong synergism, the mixtures according to the invention in all mixing ratios are considerably more active than had been predicted using Colby's formula.

USE EXAMPLE 1

Activity Against Rice Blast *Pyricularia oryzae* in the Microtiterplate Test

The stock solutions were mixed according to the ratio, pipetted onto a micro titer plate (MTP) and diluted with water to the stated concentrations. A spore suspension of *Pyricularia oryzae* in an aqueous biomalt solution was then added. The plates were placed in a water vapor-saturated chamber at a temperature of 18° C. Using an absorption photometer, the MTPs were measured at 405 nm 7 days after the inoculation.

| Active compounds/active compound compositions | Concentration [ppm] | Ratio | Observed efficacy | Calculated efficacy according to Colby (%) |
|---|---|---|---|---|
| Boscalid + Chlorothalonil | 0.25 + 0.25 | 1:1 | 23 | — |
|  | 0.063 + 0.063 | 1:1 | 0 | — |
| Epoxiconazol | 1 | — | 40 | — |
|  | 0.063 | — | 4 | — |
| Boscalid + Chlorothalonil + Epoxiconazol | 0.25 + 0.25 + 1 | 1:1:4 | 100 | 26 |
| Boscalid + Chlorothalonil + Epoxiconazol | 0.25 + 0.25 + 0.063 | 4:4:1 | 100 | 54 |
| Metconazol | 0.25 | — | 5 | — |
|  | 0.063 | — | 0 | — |
| Boscalid + Chlorothalonil + Metconazol | 0.25 + 0.25 + 0.063 | 4:4:1 | 100 | 23 |
| Boscalid + Chlorothalonil + Metconazol | 0.063 + 0.063 + 0.25 | 1:1:4 | 54 | 5 |

USE EXAMPLE 2

Activity Against *Fusarium culmorum* in the Microtiterplate Test

The stock solutions were mixed according to the ratio, pipetted onto a micro titer plate (MTP) and diluted with water to the stated concentrations. A spore suspension of *Fusarium culmorum* in an aqueous biomalt solution was then added. The plates were placed in a water vapor-saturated chamber at a temperature of 18° C. Using an absorption photometer, the MTPs were measured at 405 nm 7 days after the inoculation.

| Active compounds/active compound compositions | Concentration [ppm] | Ratio | Observed efficacy | Calculated efficacy according to Colby (%) |
|---|---|---|---|---|
| Boscalid + Chlorothalonil | 0.25 + 0.25 | 1:1 | 2 | — |
| Metconazol | 0.063 | — | 31 | — |
| Boscalid + Chlorothalonil + Metconazol | 0.25 + 0.25 + 0063 | 4:4:1 | 98 | 33 |

USE EXAMPLE 3

Activity Against *Alternaria solani* in the Microtiterplate Test

The stock solutions were mixed according to the ratio, pipetted onto a micro titer plate (MTP) and diluted with water to the stated concentrations. A spore suspension of *Alternaria solani* in an aqueous biomalt solution was then added. The plates were placed in a water vapor-saturated chamber at a temperature of 18° C. Using an absorption photometer, the MTPs were measured at 405 nm 7 days after the inoculation.

| Active compounds/active compound compositions | Concentration [ppm] | Ratio | Observed efficacy | Calculated efficacy according to Colby (%) |
|---|---|---|---|---|
| Boscalid + Chlorothalonil | 0.25 + 0.25 | 1:1 | 18 | — |
| Benthivalicarb | 4 | — | 0 | — |
| Tebuconazole | 4 | — | 0 | — |
| Boscalid + Chlorothalonil + Benthivalicarb | 0.25 + 0.25 + 4 | 1:1:16 | 42 | 18 |
| Boscalid + Chlorothalonil + Tebuconazol | 0.25 + 0.25 + 4 | 1:1:16 | 81 | 18 |

USE EXAMPLE 4

Activity Against *Colleotrichum truncatum* in the Microtiterplate Test

The stock solutions were mixed according to the ratio, pipetted onto a micro titer plate (MTP) and diluted with water to the stated concentrations. A spore suspension of *colleotrichum truncatum* in an aqueous biomalt solution was then added. The plates were placed in a water vapor-saturated chamber at a temperature of 18° C. Using an absorption photometer, the MTPs were measured at 405 nm 7 days after the inoculation.

| Active compounds/active compound compositions | Concentration [ppm] | Ratio | Observed efficacy | Calculated efficacy according to Colby (%) |
|---|---|---|---|---|
| Boscalid + Chlorothalonil | 0.25 + 0.25 | 1:1 | 11 | — |
|  | 0.063 + 0.063 | 1:1 | 0 | — |
| Fluoxastrobin | 1 | — | 32 | — |
| Boscalid + Chlorothalonil + Fluoxastrobin | 0.25 + 0.25 + 1 | 1:1:4 | 72 | 40 |
| Picoxystrobin | 0.25 | — | 32 | — |
| Boscalid + Chlorothalonil + Picoxystrobin | 0.25 + 0.25 + 0.25 | 1:1:1 | 70 | 40 |
| Azoxystrobin | 1 | — | 54 | — |
| Boscalid + Chlorothalonil + Azoxystrobin | 0.25 + 0.25 + 1 | 1:1:4 | 77 | 59 |
| Tebuconazol | 4 | — | 0 | — |
| Boscalid + Chlorothalonil + Tebuconazol | 0.25 + 0.25 + 4 | 1:1:16 | 62 | 11 |
| Benthivalicarb | 4 | — | 0 | — |
| Boscalid + Chlorothalonil + Benthivalicarb | 0.25 + 0.25 + 4 | 1:1:16 | 40 | 11 |
| Triticonazol | 1 | — | 7 | — |
| Boscalid + Chlorothalonil + Triticonazol | 0.25 + 0.25 + 1 | 1:1:4 | 45 | 17 |
| Pyrimethanil | 4 | — | 7 | — |
| Boscalid + Chlorothalonil + Pyrimethanil | 0.25 + 0.25 + 4 | 1:1:16 | 52 | 17 |
| Iprodion | 1 | — | 7 | — |
| Boscalid + Chlorothalonil + Iprodion | 0.25 + 0.25 + 1 | 1:1:4 | 35 | 17 |
| Captan | 1 | — | 49 | — |
| Boscalid + Chlorothalonil + Captan | 0.063 + 0.063 + 1 | 1:1:16 | 88 | 49 |

The invention claimed is:

1. A fungicidal composition for controlling phytopathogenic harmful fungi, comprising
   1) Boscalid,
   2) Chlorothalonil and
   3) at least one fungicidally active compound III selected from groups A) to E):
      A) an azole selected from the group consisting of cyproconazole, difenoconazole, diniconazole, enilconazole, epoxicon-azole, fluquinconazole, fenbuconazole, flusilazole, hexacon-azole, imibenconazole, ipconazole, metconazole, pencon-azole, propiconazole, prothioconazole, simeconazole, tebuconazole, and tetraconazole;
      B) a strobilurin selected from the group consisting of azoxystrobin, dimoxy-strobin, enestroburin, fluoxastrobin, kresoxim-methyl, methominostrobin, orysastrobin, picoxystrobin, pyraclostrobin, and trifloxystrobin;
      C) a heterocyclic compound selected from the group consisting of cyprodinil, mepanipyrim, pyrimethanil, iprodione, pro-cymidone, vinclozolin, captafol, captan, and folpet;
      D) a carbamate selected from the group consisting of iprovalicarb, and benthiavalicarb;
   in a synergistically effective amount, wherein boscalid, chlorothalonil and a fungicidally active compound III are present in a weight ratio of from 10:1:1 to 1:10:10, to 1:10:1, to 10:1:10.

2. The fungicidal composition according to claim 1, comprising, as fungicidally active compound III, an azole.

3. The fungicidal composition according to claim 1, comprising, as fungicidally active compound III, epoxyconazole, or fluquinconazole, metconazole.

4. A fungicidal agent comprising at least one solid or liquid carrier and a composition according to claim 1.

5. A method for controlling phytopathogenic harmful fungi, which method comprises treating the fungi, their habitat or the plants to be protected against fungal attack, the soil, seed, areas, materials or spaces the soil or the plants to be protected against fungal attack with an effective amount of the fungicidal composition of claim 1.

6. The method according to claim 5, wherein boscalid, chlorothalonil and the fungicidally active compound III are applied simultaneously, that is jointly or separately, or in succession.

7. The method according to claim 5, wherein the composition according to claim 1 is applied in an amount of from 5 g/ha to 2500 g/ha.

8. The method according to claim 5, wherein the composition according claim 1 is applied in an amount of from 1 g to 1000 g per 100 kg of seed.

9. A seed treated with the composition according claim 1 in an amount of from 1 g to 1000 g per 100 kg of seed.

10. The method of claim 5, wherein the fungicidal composition comprises, as fungicidally active compound III, epoxyconazole, fluquinconazole, metconazole or triticonazole.

11. The method of claim 8, wherein the fungicidal composition comprises, as fungicidally active compound III, epoxyconazole, fluquinconazole, metconazole or triticonazole.

12. The seed of claim 9, wherein the fungicidal composition comprises, as fungicidally active compound III, epoxyconazole, fluquinconazole, metconazole or triticonazole.

* * * * *